US005898032A

United States Patent [19]
Hodgen

[11] Patent Number: 5,898,032
[45] Date of Patent: Apr. 27, 1999

[54] ULTRA LOW DOSE ORAL CONTRACEPTIVES WITH LESS MENSTRUAL BLEEDING AND SUSTAINED EFFICACY

[75] Inventor: Gary D. Hodgen, Virginia Beach, Va.

[73] Assignee: Medical College of Hampton Roads, Norfolk, Va., VA

[21] Appl. No.: 08/880,419

[22] Filed: Jun. 23, 1997

[51] Int. Cl.$^6$ ..................................... A61K 31/56
[52] U.S. Cl. ................. 514/178; 514/170; 514/182; 514/843
[58] Field of Search ................... 514/178, 170, 514/182, 843

[56] References Cited

U.S. PATENT DOCUMENTS

| | | |
|---|---|---|
| 4,390,531 | 6/1983 | Edgren . |
| 5,098,714 | 3/1992 | Wright, et al. . |
| 5,108,995 | 4/1992 | Casper ..................................... 514/843 |
| 5,208,225 | 5/1993 | Boissonneault et al. ............... 514/843 |
| 5,552,394 | 9/1996 | Hodgen . |
| 5,756,490 | 5/1998 | Lachnit et al. ........................... 514/843 |

FOREIGN PATENT DOCUMENTS 0253607  1/1988  European Pat. Off. .

OTHER PUBLICATIONS

Sheth, et al., Contraception 25:243, 1982.
"A Randomized, Double–Blind Study of Two Combined and Two Progestogen–Only Oral Contraceptives"; Sheth, et al., Contraception; Mar. 1982 vol. 25., No. 3; pp. 243–253.

*Primary Examiner*—James H. Reamer
*Attorney, Agent, or Firm*—Ostrolenk, Faber, Gerb & Soffen, LLP

[57] ABSTRACT

A method of female contraception involves administering a combination of estrogen and progestin for 60–110 consecutive days in which the daily amounts of estrogen and progestin are equivalent to about 5–35 mcg of ethinyl estradiol and about 0.025 to 10 mg of norethindrone acetate, respectively. The advantages include less menstrual bleeding, less patient anemia, less total exposure to medication, higher compliance rates and more lifestyle convenience for patients.

11 Claims, No Drawings

ULTRA LOW DOSE ORAL CONTRACEPTIVES WITH LESS MENSTRUAL BLEEDING AND SUSTAINED EFFICACY

BACKGROUND OF THE INVENTION

The ovarian/menstrual cycle is a complex event characterized by an estrogen rich follicular phase and, after ovulation, a progesterone rich luteal phase. Each has a duration of approximately 14 days resulting in an intermenstrual interval of about 28 days. The endometrial tissue responds to the changes in hormonal milieu.

The onset of menstruation is the beginning of a new menstrual cycle and is counted as day 1. During a span of about 5 to 7 days, the superficial layers of the endometrium, which grew and developed during the antecedent ovarian/menstrual cycle, are sloughed because demise of the corpus luteum in the non-fertile menstrual cycle is associated with a loss of progesterone secretion. Ovarian follicular maturation occurs progressively resulting in a rise in the circulating levels of estrogen, which in turn leads to new endometrial proliferation.

The dominant ovarian follicle undergoes ovulation at mid-cycle, generally between menstrual cycle days 12 to 16 and is converted from a predominantly estrogen source to a predominantly progesterone source (the corpus luteum). The increasing level of progesterone in the blood converts the proliferative endometrium to a secretory phase in which the tissue proliferation has promptly abated, leading to the formation of endometrial glands or organs. When the ovulated oocyte is viably fertilized and continues its progressive embryonic cleavage, the secretory endometrium and the conceptus can interact to bring about implantation (nidation), beginning about 6 to 8 days after fertilization.

If an ongoing pregnancy is to be established via implantation, the embryo will attach and burrow into the secretory endometrium and begin to produce human chorionic gonadotropin (HCG). The HCG in turn stimulates extended corpus luteum function, i.e. the progesterone production remains elevated, and menses does not occur in the fertile menstrual cycle. Pregnancy is then established.

In the non-fertile menstrual cycle, the waning level of progesterone in the blood causes the endometrial tissue to be sloughed. This starts a subsequent menstrual cycle.

Because endometrial proliferation serves to prepare the uterus for an impending pregnancy, manipulation of hormones and of the uterine environment can provide contraception. For example, estrogens are known to decrease follicle stimulating hormone secretion by feedback inhibition. Under certain circumstances, estrogens can also inhibit luteinizing hormone secretion, once again by negative feedback. Under normal circumstances, the spike of circulating estrogen found just prior to ovulation induces the surge of gonadotropic hormones that occurs just prior to and resulting in ovulation. High doses of estrogen immediately postcoitally also can prevent conception probably due to interference with implantation.

Progestins can also provide contraception. Endogenous progesterone after estrogen is responsible for the progestational changes of the endometrium and the cyclic changes of cells and tissue in the cervix and the vagina. Administration of progestin makes the cervical mucus thick, tenacious and cellular which is believed to impede spermatozoal transport. Administration of progestin also inhibits luteinizing hormone secretion and blocks ovulation in humans.

The most prevalent form of oral contraception is a pill that combines both an estrogen and a progestin, a so-called combined oral contraceptive preparation.

Alternatively, there are contraceptive preparations that comprise progestin only. However, the progestin-only preparations have a more varied spectrum of side effects than do the combined preparations, especially more breakthrough bleeding. As a result, the combined preparations are the preferred oral contraceptives in use today (Sheth et al., *Contraception* 25:243, 1982).

Whereas the conventional 21 day pill packs with a 7 day "pill free" or placebo interval worked well when oral contraceptives were of higher dosage, as the doses have come down, for both the estrogen and progestin components, bleeding problems have increased in frequency, especially in the early months of oral contraceptive use, but even persistently so in some patients.

Since the advent of combined estrogen-progestin medications as oral contraceptives, there has been a steady downward adjustment of the daily estrogen dosage. Concurrently, where exposure to the progestin component has also been lowered, reduced androgenicity has remained an ongoing priority. Together these adaptions in formulation have been presented in a variety of regimens, both monophasic and multiphasic. Each have their own advantages and disadvantages. All-in-all, today's oral contraceptives are much safer with regard to the incidence and severity of estrogen-linked clotting disorders as well as the suggested cumulative impact of more "lipid friendly" progestins that maintain the potentially advantageous high density lipoprotein cholesterol levels in circulation.

U.S. Pat. No. 4,390,531 teaches a triphasic regimen in which each phase uses about 20–40 mcg ethinyl estradiol, phases 1 and 3 use 0.3–0.8 norethindrone and phase 2 doubles the amount of the norethindrone. These three phases consume 21 days of a 28 day cycle. European published application 0 226 279 states that this regimen is associated with a high incidence of breakthrough bleeding and substitutes a three phase oral contraceptive regimen using a relatively low amount of ethinyl estradiol (10–50 $\mu$g) and a relatively high amount of norethindrone acetate (0.5–1.5 mg) in each phase provided that the amount of estrogen in any two phases is never the same. A "rest" phase of about 7 days is used in this regimen.

U.S. Pat. No. 5,098,714 teaches an osmotic, oral dosage form. One "pill" is administered per day but the administration is, in effect, polyphasic. The dosage form is constructed such that it provides an initial pulse delivery of estrogen and progestin followed by prolonged delivery of estrogen.

European published patent application 0 253 607 describes a monophasic contraceptive preparation containing units having 0.008–0.03 mg of ethinyl estradiol and 0.025–0.1 mg of desogestrel (or equivalent) and a regimen where the preparation is administered over a 23–25 day period, preferably 24 days, followed by a 2–5 day pill-free period. The object of this regimen is to provide hormonal replacement therapy and contraceptive protection for the pre-menopausal woman in need thereof by supplying a low dose of an estrogen combined with a "very low dose of a progestogen."

In 1989, the accumulating data from the evolution of oral contraceptive pill formulations containing only 20–35 $\mu$g of estrogen per day spurred the Food and Drug Administration's Fertility and Maternal Health Drugs Advisory Committee to recommend indication of low dose oral contraceptives for healthy, non-smoking women even during the perimenopausal years, such as, for instance, ages 35–50. In Japan, oral contraceptives are being evaluated for safety and efficacy, as well as social acceptability, for the first time.

U.S. Pat. No. 5,552,394 describes a method of female contraception which is characterized by a reduced incidence of breakthrough bleeding after the first cycle involves monophasicly administering a combination of estrogen and progestin for 23–25 consecutive days of a 28 day cycle in which the daily amounts of estrogen and progestin are equivalent to about 5–35 mcg of ethinyl estradiol and about 0.025 to 10 mg of norethindrone acetate, respectively and in which the weight ratio of estrogen to progestin is at least 1:45 calculated as ethinyl estradiol to norethindrone acetate.

In establishing a estrogen-progestin regimen for oral contraceptives, two principal issues must be confronted. First, efficacy must be maintained and second, there must be avoidance of further erosion in the control of endometrial bleeding. In general, even the lowest dose oral contraceptive products commercially available have demonstrated efficacy but the overall instances of bleeding control problems has increased as the doses were reduced, as manifest both in breakthrough bleeding (untimely flow or spotting) or withdrawal amenorrhea during the "pill free" week (expected menses).

It is the object of the present invention to provide a new estrogen-progestin combination and/or regimen for oral contraceptive use which maintains the efficacy and provides enhanced control of endometrial bleeding. The regimen enhances compliance by involving fewer stop/start transitions per year and also results in less blood loss in patients with anemia. Having fewer menstrual intervals can enhance lifestyles and convenience. This and other objects of the invention will become apparent to those skilled in the art from the following detailed description.

SUMMARY OF THE INVENTION

This invention relates to a method of female contraception which is characterized by a reduced number of withdrawal menses per year. More particularly, it relates to a method of female contraception which involves administering, preferably monophasicly, a combination of estrogen and progestin for 60–110 consecutive days followed by 3–10 days of no administration, in which the daily amounts of the estrogen and progestin are equivalent to about 5–35 mcg of ethinyl estradiol and about 0.025–10 mg of norethindrone acetate, respectively.

DESCRIPTION OF INVENTION

In accordance with the present invention, a women in need of contraception is administered a combined dosage form of estrogen and progestin, preferably monophasicly, for 60 to 110 consecutive days, preferably about 80–90 days, followed by an administration free interval of 3 to 10 days, preferably about 5–8 days, in which the daily amounts of estrogen and progestin are equivalent to about 5–35 mcg of ethinyl estradiol and about 0.025 to 10 mg of norethindrone acetate, respectively. On a schedule of 84 days administration followed by 7 pill free days, there are only four treatment and menstrual cycles per year.

The preferred estrogen and progestins are ethinyl estradiol and norethindrone acetate although other estrogens and progestins can be employed. The weight ratio of these two active ingredients is at least 1:45 and preferably at least 1:50. The preferable amount of ethinyl estradiol is about 10–20 mcg and the preferable amount of the norethindrone acetate is about 0.25–1.5 mg. Other estrogens vary in potency from ethinyl estradiol. For example, 30 mcg of ethinyl estradiol is roughly equivalent to 60 mcg of mestranol or 2,000 mg of 17 β-estradiol. Likewise, other progestins vary in potency from norethindrone acetate. Thus, 3.5 mg of norethindrone acetate is roughly equivalent to 1 mg of levonorgestrel or desogestrel and 3-ketodesogestrel and about 0.7 mg of gestodene. The values given above are for the ethinyl estradiol and the norethindrone acetate and if a different estrogen or progestin is employed, an adjustment in the amount based on the relative potency should be made. The correlations in potency between the various estrogens and progestins are known.

Other useable estrogens include the esters of estradiol, estrone and ethinyl estradiol such as the acetate, sulfate, valerate or benzoate, conjugated equine estrogens, agnostic anti-estrogens, and selective estrogen receptor modulators. The estrogen is administered in the conventional manner by any route where it is active, for instance orally or transdermally. Most estrogens are orally active and that route of administration is therefore preferred. Accordingly, administration forms can be tablets, dragees, capsules or pills which contain the estrogen (and preferably the progestin) and a suitable pharmaceutically acceptable carrier.

Pharmaceutical formulations containing the progestin and a suitable carrier can be solid dosage forms which includes tablets, capsules, cachets, pellets, pills, powders or granules; topical dosage forms which includes solutions, powders, fluid emulsions, fluid suspensions, semi-solids, ointments, pastes, creams, gels or jellies, foams and controlled release depot entities; and parenteral dosage forms which includes solutions, suspensions, emulsions or dry powder comprising an effective amount of progestin as taught in this invention. It is known in the art that the active ingredient, the progestin, can be contained in such formulations in addition to pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, "Modern Pharmaceutics", Banker & Rhodes, Marcel Dekker, Inc. 1979; "Goodman & Gilman's The Pharmaceutical Basis of Therapeutics", 6th Edition, MacMillan Publishing Co., New York 1980 can be consulted.

The pharmaceutical formulations may be provided in kit form containing at least about 60, and preferably at least about 84 tablets, and up to 110 tablets, intended for ingestion on successive days. Preferably administration is daily for at least 60 days using tablets containing the both the estrogen and the progestin and then for at least 3 days with placebo.

In order to further illustrate the present invention, specific examples are set forth below. It will be appreciated, however, that these examples are illustrative only and are not intended to limit the scope of the invention.

EXAMPLE 1

A study is carried out at a fully accredited animal research facility which complies through its animal care and use committee with the review standards set forth in the National Institute of Health's "Guide for Care and Use of Laboratory Animals", the Public Health Services' "Principles for the Care and Use of Laboratory Animals", and the United States Department of Agriculture's Implementation Regulations of the 1985 Amendments for the Animal Welfare Act.

Ten adult female cynomolgus monkeys (*macaca fasicularis*) having regular presumably ovulatory menstrual cycles (28.9±3.1 days for the month prior to study entry) are selected. Their duration of spontaneous menses is 3.4±1.4 days. Mean body weight of the monkeys is 4.9±1.1 kg (X ±SEM). They are housed individually in a controlled environment (12 hours of light and 23° C.). Their diet is a commercial primate food (Purina, St. Louis, Mo.) with water ad libitum.

The monkeys are divided at random into two groups (N=5 each). The studies begin with spontaneous menstruation in a pretreatment control cycle. At the onset of the next spontaneous menses, alternatively, they are assigned to receive on cycle day one an ultra low dose oral contraceptive for either 60 consecutive days, followed by 3 non-treatment days or 84 consecutive days, followed by a 7 non-treatment days. These regimens are continued through three treatment cycles. The study concludes with each group of primates being followed during a post-treatment spontaneous ovarian menstrual cycle.

Femoral blood is collected daily and the serum frozen for subsequent RIA of estradiol, progesterone, FSH and LH in the pretreatment and post-treatment cycles and every 3rd day during all three treatment cycles, except daily through the "pill free" interval. Bleeding profiles are kept by daily vaginal swabs, indicating spontaneous menstruation, withdrawal bleeding, breakthrough bleeding, or withdrawal amenorrhea. Breakthrough bleeding is defined as detectable blood in the vagina outside of the first 8 days after the last dose of oral contraceptive or the onset of spontaneous menses in non-treatment cycles.

Since the objective is to test an ultra low dose oral contraceptive, the medication is adjusted to fit the smaller (than human) body weight of these laboratory primates. The dose of ethinyl estradiol is 1.2 μg/day, while the dose of norethindrone acetate is 0.06 mg/day. This "in-house" reformulation is achieved by grinding to powder a commercially available monophasic pill (Loestrin 1/20, Parke Davis, Morris Plains, N.J.), which originally contained 1 mg of norethindrone acetate and 20 μg of ethinyl estradiol per tablet, contained in a conventional 21 day pack along with 7 iron-containing placebos.

In terms of comparison to human dose equivalents, the daily dose received by the monkeys (with a monkey's body weight about 5 kg and a woman's at 50 kg) is about 12 μg of ethinyl estradiol and 0.6 mg of norethindrone acetate. Thus, this ultra low dose oral contraceptive formulation presented a 40% reduction in daily estrogen-progestin exposure as compared to one of the lowest estrogen dose combination oral contraceptives commercially available today in America or Europe. Taking into account that when a continuous 84 day ultra low dose regimen plus a 7 dy pill free interval was used, versus the traditional 21+7 day protocol, that there would be 63 more doses on an annualized basis, still the exposure to medication was reduced by more than 26% yearly, compared to the commercial product Loestrin 1/20.

EXAMPLES 2–5

The example 1 procedure is repeated using the following combinations of estrogen and progestin:

| Example | Estrogen | Progestin | Treatment Days |
|---|---|---|---|
| 2 | mestranol | levo-norgestrel | 84 |
| 3 | 17-beta-estradiol | 3-keto-desogestrel | 110 |
| 4 | ethinyl estradiol | desogestrel | 80 |
| 5 | mestranol | gestodone | 60 |

Application of the compounds, compositions and methods of the present invention for the medical or pharmaceutical uses described can be accomplished by any clinical, medical, and pharmaceutical methods and techniques as are presently or prospectively known to those skilled in the art. It will therefore be appreciated that the various embodiments which have been described above are intended to illustrate the invention and various changes and modifications can be made in the inventive method without departing from the spirit and scope thereof.

What is claimed is:

1. A method of female contraception which comprises monophasicly administering to a pre-menopausal female a combination of estrogen and progestin for 60–110 consecutive days in which the daily amounts of estrogen and progestin are equivalent to about 5–35 mcg of ethinyl estradiol and about 0.025 to 10 mg of norethindrone acetate, respectively, following by non-administration for a period of 3–10 days.

2. The method of claim 1 in which the daily amount of estrogen is equivalent to about 10 to 20 mcg of ethinyl estradiol.

3. The method of claim 2 in which the daily amount of progestin is equivalent to 0.25–1.5 mg of norethindrone acetate.

4. The method of claim 3 in which the combination is administered for at least 80 consecutive days.

5. The method of claim 4 in which the estrogen is ethinyl estradiol.

6. The method of claim 5 in which the progestin is norethindrone acetate.

7. The method of claim 1 in which the daily amount of progestin is equivalent to 0.25–1.5 mg of norethindrone acetate.

8. The method of claim 1 in which the combination is administered for at least 80 consecutive days.

9. The method of claim 1 in which the estrogen is ethinyl estradiol.

10. The method of claim 1 in which the progestin is norethindrone acetate.

11. The method of claim 1 in which the daily amount of estrogen is up to 30 mcg of ethinyl estadiol.

* * * * *